US011638702B2

(12) United States Patent
Hashim

(10) Patent No.: US 11,638,702 B2
(45) Date of Patent: *May 2, 2023

(54) GLYCERYL 3-HYDROXYBUTYRATES FOR TRAUMATIC BRAIN INJURY

(71) Applicant: NeuroEnerygy Ventures, Inc., New York, NY (US)

(72) Inventor: Sami Hashim, Dobbs Ferry, NY (US)

(73) Assignee: NeuroEnerygy Ventures, Inc., New York, NY (US)

( * ) Notice: Subject to any disclaimer, the term of this patent is extended or adjusted under 35 U.S.C. 154(b) by 506 days.

This patent is subject to a terminal disclaimer.

(21) Appl. No.: 16/897,349

(22) Filed: Jun. 10, 2020

(65) Prior Publication Data

US 2020/0297686 A1    Sep. 24, 2020

Related U.S. Application Data

(63) Continuation of application No. 15/909,240, filed on Mar. 1, 2018, now Pat. No. 10,736,867, which is a continuation of application No. 15/404,396, filed on Jan. 12, 2017, now Pat. No. 9,925,164.

(51) Int. Cl.
 *A61K 31/225*      (2006.01)
(52) U.S. Cl.
 CPC .................................. *A61K 31/225* (2013.01)
(58) Field of Classification Search
 CPC combination set(s) only.
 See application file for complete search history.

(56) References Cited

U.S. PATENT DOCUMENTS

| | | | |
|---|---|---|---|
| 6,136,862 | A | 10/2000 | Hiraide et al. |
| 6,323,237 | B1 | 11/2001 | Veech |
| 7,807,718 | B2 | 10/2010 | Hashim |
| 8,748,400 | B2 | 6/2014 | Henderson |
| 9,138,420 | B2 | 9/2015 | D'Agostino et al. |
| 9,364,456 | B1 | 6/2016 | Weeber et al. |
| 2008/0058416 | A1 | 3/2008 | Greenwood et al. |
| 2010/0197758 | A1 | 8/2010 | Andrews et al. |
| 2011/0237666 | A1 | 9/2011 | Clarke et al. |
| 2012/0034193 | A1 | 2/2012 | Rees et al. |
| 2014/0072654 | A1 | 3/2014 | D'Agostino et al. |
| 2014/0073693 | A1 | 3/2014 | D'Agostino et al. |
| 2014/0350105 | A1 | 11/2014 | D'Agostino et al. |
| 2015/0231172 | A1 | 8/2015 | D'Agostino et al. |
| 2016/0067207 | A1 | 3/2016 | D'Agpostino et al. |
| 2016/0078782 | A1 | 3/2016 | Meidenbauer |
| 2016/0317487 | A1 | 11/2016 | D'Agostino et al. |
| 2017/0000754 | A1 | 1/2017 | Weeber et al. |
| 2017/0196827 | A1 | 7/2017 | Veech et al. |
| 2017/0258745 | A1 | 9/2017 | Millet |
| 2017/0266148 | A1 | 9/2017 | D'Agostino et al. |
| 2017/0290792 | A1 | 10/2017 | Cavaleri |
| 2017/0296501 | A1 | 10/2017 | Lowery |
| 2018/0021274 | A1 | 1/2018 | Arnold |
| 2018/0055797 | A1 | 3/2018 | Llosa et al. |
| 2018/0057846 | A1 | 3/2018 | Llosa et al. |
| 2019/0091189 | A1 | 3/2019 | D'Agostino et al. |

FOREIGN PATENT DOCUMENTS

| | | |
|---|---|---|
| FR | 2997302 A1 | 5/2014 |
| JP | 1998 095730 | 4/1998 |
| JP | 2008-542298 | 11/2008 |
| JP | 2009 173766 A | 8/2009 |
| JP | 2015-042644 A | 3/2015 |
| WO | 1998041200 A1 | 9/1998 |
| WO | 2006128006 A1 | 11/2006 |
| WO | 2011101171 A1 | 8/2011 |
| WO | 2015034812 A2 | 3/2015 |
| WO | 2017011294 A1 | 1/2017 |
| WO | 2018009208 A1 | 1/2018 |
| WO | 2018049383 A1 | 3/2018 |

OTHER PUBLICATIONS

AMEDD Centers School—Chapters Traumatic Brain Injury pages Mar. 2017 345-391 http:/fwww.cs.amedd.army.mil/borden/book/ccc/uclachp8.pdf.
Balietti et al; Ketogenic diets: An historical antiepiletic therapy with promising potentiualities for the aging brain; Aging Research and Reviews 9 (2010) 273-279.
Bengsch; Less carbs, more fat: ketogenic diet makes migraine patient's headaches disappear; Oct. 14, 2016.
Steven P. Broglio, et al.; National Athletic Trainers' Association Position Statement Management of Sport Concussion; Journal of Athletic Training 2014;49(2):245-265.
Cahill; President's address: Starvation; Trans Am Clin Climatol; Assoc 94:1-21, 1983.
Center for Disease Control and Prevention—Updated Mild Traumatic Brain Injury Guideline for Adults https://www.cdc.gov/traumaticbraininjury/mtbi_guideline.html.
Clarke et al; Kinetics, safety and tolerability of (R)-3-hydroxybutyryl (R)-3-hydroxybutyrate in healthy adult subjects; Regul Toxicol Pharmacol 63: 401-408, 2012.
Dept. of Surgical Education, Orlando Regional Medical Center—Severe Traumatic Brain Injury Management http://www.surgicalcriticalcare.net/Guidelines/Severe%20TBI%202017.pdf May 4, 2017 (latest revision).
Dept. of Veteran Affairs/Dept of Defense—Management of Concussion/mild Traumatic Brain Injury 2009 https://www.healthquality.va.gov/guidelines/Rehab/mtbi/concussion_mtbi_full_1 _0.pdf.
Department of Emergency Medicine Education , University of Texas Southwestern Medical Center, Dallas—Evidence-based Guidelines for Adult Traumatic Brain Injury Care 2010 http://www jems.com/articles/print/volume-35/issue-4/patient-care/evidence-based-guidelines-adul.html.
Di Lorenzo, et la; Cortical function correlates of responsiveness to short-lasting preventive intervention with ketogenic diet in migraine: a multimodal evoked potential study; J Headache Pain 17: 58-67, 2016.

(Continued)

*Primary Examiner* — Kathrien A Hartsfield
(74) *Attorney, Agent, or Firm* — Irving M. Fishman

(57) ABSTRACT

A method of treatment of mild to moderate non-penetrating closed traumatic brain injury and mild to moderate TBI due to surgical intervention using 3-hydroxybutyate glycerides is disclosed.

9 Claims, No Drawings

(56) References Cited

OTHER PUBLICATIONS

Di Lorenzo et al; Diet transiently improves migraine in two sisters: possible role of ketogenesis?; Funct. Neurol. Oct.-Dec. 2013; 23 (4):305-308 Published online at https:/www.ncbi.nlm.nih.gov/pmc/articles/PMC3951260/.
Di Lorenzo et al; Migraine improvement during short lasting ketogenesis: a proof-of-concept study; European J Neurology 2015, 22:170-177.
Faul et al; Traumatic Brain Injury in the United States: Emergency Department Visits, Hospitalizatiojns and Deaths 2002-2006.; Centers for Disease Control and Prevention National Center for Injury Prevention and Control, Atlanta, GA (Mar. 2010); http://www.cdc.gov/TraumaticBrainInjury/.
Fuehrlein, et al; Differential metabolic effects of saturated versus polyunsaturated fats in ketogenic diets; J Clin Endocrinol Metab 89:1641-1645, 2004.
Gasier et al; Neuroprotective and disease-modifyingeffects of the ketogenic diet; Behav. Pharmacol Sep. 17, 2006 (5-6) 431-439.
Guidelines for the Management of Severe Traumatic Brain Injury, 4th ed., 2016, pp. 1-244 https://braintrauma.org/uploads/03/12/Guidelines_for_Management_of_Severe_TBI_4th_Edition.pdf.
Hashim et al; Ketone body therapy: from the ketogenic diet to the oral administration of ketone ester; J Lipid Res 55:1818-1826, 2014.
HHS Agency for Healthcare Research and Quality—Traumatic brain injury medical treatment guidelines 2012 https://guideline.gov/summaries/summary/43752/Traumatic-brain-injury-medical-treatment-guidelines.
Huttenlocher, et al; Medium-Chain triglycerides as a therapy for intractable childhood epilepsy; Neurology, vol. 11, Nov. 1971, 1097-1103.
Institute of Medicine (US) Committee on Nutrition, Trauma, and the Brain; Erdman J, Oria M, Pillsbury L, editors. Nutrition and Traumatic Brain Injury: Improving Acute and Subacute Health Outcomes in Military Personnel. Washington (DC): National Academies Press (US); Apr. 11, 2011., Ketogenic Diet. Retrieved from internet on Jun. 26, 2017 from: www.iom.edu/tbinutrition.
Kossoff et al.; Ketogenic Diets: New Advances for Metabolism-Based Therapies. Current Opinion in Neurology. Apr. 2012, vol. 25, No. 2, pp. 173-178.
Newport et al; A new way to produce hyperketonemia: Use of ketone ester in a case of Alzheimer's disease; Alzheimer's and Dimentia 2014: 1-5, Elsevier.
Prins. Cerebral metabolic adaptation and ketone metabolism after brain injury; published online 2007; https://www.ncbi.nlm.nih.gov/pmc/articles/PMC2857668/[ J Cereb Blood Flow Metab 200 Jan 20(1) 1-16 https://dx.doi org/10.1038%2Fsj.jcbfm.9600543.
Prins et al; The collective potential of cerebral ketone metabolism in traumatic brain injury; J Lipid Res 55:2450-2457, 2014.
Prins et al; Increased cerebral uptake and oxidation of endogenous beta HB improves ATP following traumatic brain injury; J Neurochem 90: 666-672, 2004.
Rainero et al; Insulin Sensitivity is impaired in patients with migraine; Cephalagia 25:593-597, 2005 (Abstract).
Ritter et al; Evaluation of a carbohydrate-free diet fir patients with severe head injury; J Neurotrauma 13:475-485, 1996.
Salame et al—Ketogenic neuroprotection of Repeat TBI in Juvenile Rats—J Neurotrauma 2012 Abstract.
Teasdale; Assessment of Coma and Impaired Consciousness: A Practical Scale; The Lancet, Jul. 13, 1974, pp. 81-84.
University of Mississippi Medical Center, Section of Neurotrauma, Dept. of Neurosurgery—Guidelines for the Critical Dare Management of Severe Head Injury 2008 pp. 1-32 https://www2.umc.edu/uploadedFiles/UMCedu/Content/Education/Schools/Medicine/Clinical_Science/Neurosurgery/Clinical_Services/TBIGuidelines2008.pdf.
US Special Operations Command—Tactical Combat Casualty Care Guidelines 2014 http://www.itstactical.com/wp-content/uploads/2014/07/TCCC-Guidelines-update-june-2-2014.pdf.
VanItallie, et al; Ketone metabolism's ugly duckling; Nutr Rev 61:327-341, 2003.
Wheless; History and Origin of the Ketogenic Diet; pp. 31-50 from Epilepsy and the ketogenic diet (Stafstrom & Rho Editors, Humana Press Inc., Totowa, NJ).
Wilberger; Sports Related Concussion; MerckManual Professional Version online at http://www.merck.manuals.com/professional/injuries-poisining/traumatic-brain-injury-tbi/sports-related-concussion last full revision Oct. 2013.
Wilberger; Traumatic Brain Injury; Merck Manual Professional Version online at http://www.merckmanuals.com/professional/injuries-poisoning/traumatic-brain-injury-tbi/traumatic-brain-injury last full revision Oct. 2013.
Wu, et al; Medium-Chain Triglycerides in Infant Formulas and their relation to Plazma Ketone Body Concentrations; Pediatric Research, vol. 20, No. 4, 338-341, 1986.
Sekara, Fermentation production of industrial raw materials by the marine baxterium Halomonas from Okinawa; Okinawa Industrial Technology Center Report 21, 2018, pp. 1-6 with English translation of Abstract and English translation of first Paragraph (total 8 pages).
Nakamura et al, New focus on infant anesthesia—in view of growth and development—Pharmacokinetics and Pharmacodynamics; The Journal of Japan Society for Clinical Anesthesia vol. 29, No. 7, 2009 pp. 789-796 inclusive of English Abstract; plus translation of p. 1 paragraph 1, Boxed area (total 9 pages).
Veech; Hypothesis, The Mitochondrial Permeability Transition Pore Provides a Key to the Diagnosis and Treatment of Traumaic Brain Injury; IUBMB 2912, vol. 64, No. 2, 203-207.
White, et al; Clinical review: Ketones and brain injury; Critical Care 2011, 15:219 (10 pages).
Extended Search Report from European Corresponding Application dated Nov. 10, 2020 (12 pages).
Blesa, Neuroscience 2012 Presentation; Glyceryl tris-3-hydroxybutyrate protects dopaminergic neurons in a MPTP model of Parkinson's Disease; Abstract.
Shi; Review: Traumatic brain injury and hyperglycemia, a potentially modifiable risk factor; Oncotarget, 2016, vol. 7, No. 43, pp. 71052-71061.
Maxwell, et al; The impact of measurement of respiratory quotient by indirect calorimetry on the achievement of nitrogen balance in patients with severe traumatic brain injury; Eur J Trauma Emerg Surg (2017) 43:775-783.

GLYCERYL 3-HYDROXYBUTYRATES FOR TRAUMATIC BRAIN INJURY

CROSS-REFERENCE TO RELATED APPLICATIONS

This application is a continuation of U.S. patent application Ser. No. 15/909,240, filed Mar. 1, 2018, which is a continuation of U.S. patent application Ser. No. 15/404,396, filed Jan. 12, 2017, now U.S. 9,925,164, each of which is incorporated herein by reference in its entirety.

STATEMENT REGARDING FEDERALLY SPONSORED RESEARCH OR DEVELOPMENT

Not Applicable

FIELD OF THE INVENTION

The present invention is directed to the field of traumatic brain injury treatments. The invention further relates to the field of ketone bodies and further to ketone bodies in the form of 3-hydroxybutyrate glycerides, in particular, to the use of these glycerides without the maintenance of a ketogenic diet or starvation, and most particularly with concurrent feeding of a standard diet having a considerable proportion of glucogenic calorie sources such as carbohydrate.

BACKGROUND OF THE INVENTION

Traumatic brain injury (TRI) is a common disorder with an actual incidence of over 1:1 million new cases a year (Faul et al, *Traumatic Brain Injury in the United States: Emergency Department Visits, Hospitalizations and Deaths 2002-2006*, Centers for Disease Control and Prevention, National Center for Injury Prevention and Control, Atlanta, Ga. Available at http://www.cdc.gov/Traumatic Brain Injury/). TBI affects both genders across all age groups and can cause both short term and long term disabilities. In 2011, the Department of Defense (DoD) asked the Institutes of Medicine (IOM) to convene an expert committee to review the potential role of nutrition in the treatment and resilience against TBI. The IOM report (*Nutrition and Traumatic Brain Injury*, available at www.iom.edu/tbinutrition) explored the subject of nutrition and TBI and proposed certain areas of nutrition research that are promising in terms of treatment for the disorder. The IOM committee identified one promising solution that can immediately improve treatment efforts, namely early feeding of diets adequate in their level of energy and protein. The committee also suggested that more research be conducted to target potential nutritional interventions that fall into restoration of cellular energy processes, reduction in oxidative stress and inflammation, and recovery of brain function. The committee emphasized the importance of nutritional research to deal with TBI which, in one estimate 10-20% of returning veterans have sustained the disorder, while another estimate suggests that TBI accounts for up to one-third of combat related injuries. When civilian cases of TBI are added, the total number of TBI is indeed staggering.

Since the IOM Committee Report was published, a whole series of research publications have appeared to indicate that ketone bodies are useful in the treatment of neurodegenerative diseases such as Alzheimer's Parkinson's disease, amylotrophic lateral Sclerosis (ALS) and epilepsy. In order to achieve levels of plasma ketones that are therapeutic (2 mM to 7 mM) but not so high so as to produce acidosis, various investigators utilized the ketogenic diet or starvation to achieve "physiologic" or "therapeutic" ketosis (i.e. plasma ketone levels within the 2 mM to 7 mM range. The uses of the ketogenic diet(s) to treat neurodegenerative disorders are discussed in a recent review by Hashing and Van Itakkie (*Ketone body therapy: from the ketogenic diet to the oral administration of ketone ester*, J Lipid Res. 55:1818-1926, 2014). Another ester of beta-hydroxybutyrate (R-3-hydroxybutyl R-3-hydroxybutyrate) was studied as an oral supplement to induce therapeutic ketosis in healthy adult subjects (Clarke, et al. *Kinetics, safety and tolerability of (R-3-hydroxybutyl (R)-3-hydroxybutyrate in healthy adult subjects*, Regul Toxicol Pharmacol 63:401-408, 2012), and later used to treat a patient with Alzheimer's disease, with noticeable improvements in symptoms (Newport et al, *A new way to produce hyperketonemia: Use of ketone ester in a case of Alzheimer's disease*. Alzheimer's and Dementia 2014:1-5, Elsevier) without resort to the ketogenic diet or carbohydrate caloric restriction.

The role of ketone body metabolism in TBI was first studied in experimental animals. There is evidence that administration of a ketogenic diet immediately after the first concussive injury (injury that produces no cell loss) improves cognitive function after the second concussive injury (Salame, et al, *Ketogenic neuroprotection of repeat TBI in juvenile rats*, Soc Neurotrauma 2012). In the same study, rats receiving the ketogenic diet for the 24 hr interval between the two concussive injuries showed better cognitive performance. Thus, based on this reference, one would understand that carbohydrate restriction in connection with elevated ketone levels is desired and failure to restrict, carbohydrate intake is contraindicated, Further, in Gasior et al. (*Neuroprotective and disease-modifying effects of the ketogenic diet*, Behav. Pharmacal. 2006 Sep. 17(5-6) 431-439), the authors note that the beneficial effects in treating epilepsy with a ketogenic diet were quickly reversed when a high carbohydrate meal was introduced.

In TBI, there is disruption of glucose metabolism by the brain characterized by a decrease in glucose uptake, decreased glycolysis, increased glucose use by the phosphate pathway, decreased ATP production, and increased oxidative damage. Providing ketones for the brain to use (through starvation, the ketogenic diet(s), or ketone ester administration) results in a more rapid entry of the ketones into the tricarboxylic acid (TCA) cycle, a decrease in mitochondrial free radical production, an increased energy production via ATP, and increased glutathione peroxidase activity. Thus, the availability of ketone bodies in TBI compensates for the loss of energy resulting from TBI-induced diminished energy production from glucose. That the brain takes up ketones and utilizes them after controlled TBI has been demonstrated. Intravenous infusions of $^{14}$C-3-beta-hydroxybutyrate three hours following controlled concussive injury (CCI) in adult rats resulted in a greater cerebral uptake of the ketone with greater production of $^{14}CO_2$ and ATP (Prins, et al; *Increased cerebral uptake and oxidation of exogenous beta HB improves ATP following traumatic brain injury*, J. Neurochem 90: 666-672, 2004). A 1996 article (Ritter, et al, *Evaluation of a carbohydrate-free diet for patients with severe head injury*, J Neurotrauma 473485, 1996) reviews a variety of animal models of TBI that have benefited from caloric deprivation or a ketogenic diet. The authors state that clinical trials are sorely needed in view of the extensive preclinical evidence that the ketogenic diet that induces hyperketonemia (up to 7 mM) is effective in treating TBI thus rendering ketone bodies available for the brain. In a study involving 20 adult patients with severe TBI, the patients were randomized to receive either standard enteral feed or a ketogenic diet (Ritter 1996, above). Those receiving the ketogenic diet demonstrated higher ketone body levels, lower blood lactate, and better urinary nitrogen balance. The authors noted that the ketogenic diet was associated with consistent euglycemia whereas several episodes of hyperglycemia occurred in the group receiving the standard nutritional diet. Hyperglycemia has been associated with poorer outcome in patients with TBI, implying that the ketogenic diet was protective of hyperglycemia.

In a recent "thematic" review (Prins, et al. *The collective therapeutic potential of cerebral ketone metabolism in traumatic brain injury,* J Lipid Res 55: 2450-2457, 2014), the authors call for further studies to determine the optimal method to induce cerebral ketone metabolism in post injury brain. In this review the authors emphasize an initial surge in glucose metabolism soon after TBI, followed by a prolonged period of glucose metabolic depression. Ketones are the only endogenous fuel that can contribute significantly to energy production during a period of depressed glucose-derived energy. The resulting inability of the injured neurons to utilize the glucose results in homeostatic signals being generated to produce additional glucose from glycogen and also to produce additional insulin for suitable cell uptake, but the injured neurons still can't use either, so that hyperglycemia is persistent in the post injury condition.

In summary, there is extensive evidence for the beneficial role of ketogenic diet in TBI, particularly in experimental animals. However, unlike other conditions in which the use of ketogenic diets, starvation and the use of esters that are ketogenic, where glucogenic caloric intake is of no concern, the persistent hyperglycemia shown to be present in TBI, and the association of poorer outcomes in TBI the greater the hyperglycemia, leave only the ketogenic diet and starvation as the only diet driven treatments. Notwithstanding the above, Rainero et al, *Insulin sensitivity is impaired in patients with migraine,* Cephalagia 25:593-597, 2005, reported on twins with a high frequency of migraine headaches who improved during a ketogenic diet. The authors hypothesize the pathogenesis of migraine headache to diminished insulin sensitivity in the brain with consequent diminished utilization of glucose as a source of energy. Rainero states: "Our data show that insulin sensitivity is impaired in migraine and suggest a role for insulin resistance in the comorbidity between migraine and vascular disease." Rainero however shows only a coincidence of diminished ketone glucose utilization in the brain, but not any issue of hyperglycemia that needs to be contended with.

The ketogenic diet involves severe restriction of carbohydrates and includes a high proportion of fats. As cited by Gasior et al. in *Neuroprotective and disease-modifying effects of the ketogenic diet,* Behav. Pharmacol. 2006 Sep. 17 (5-6) 431-439), the first ketogenic diet was published in 1921 by Wilder (*The effects of ketonemia on the course of epilepsy,* Mayo Bull 2:307-308, 1920 relating to the treatment of children with epilepsy that is resistant to the then available pharmacologic therapies. In terms of energy distribution, the original ketogenic diet was 90% fat, 8% protein, and 2% carbohydrate.

The ketogenic diet mimics the metabolic state of total starvation. Both result in hyperketonemia of approximately the same degree, with blood ketone body levels of 2-7 mM (Cahill, *President's address: Starvation;* Trans Am Clin Climatol Assoc, 94:1-21, 1983). It is important to emphasize that this degree of hyperketonemia is fully buffered in the circulation, does not induce acidosis, and has been termed as "physiologic" or "therapeutic" ketosis (Hashim, et al; *Ketone body therapy: from the ketogenic diet to the oral administration of ketone ester;* J Lipid Res 44:1818-1826, 2014).

The ketogenic diet is not the most pleasant of diets. It is rather difficult to follow, and when followed, it can produce rises in LDL cholesterol, in uric acid, and free fatty acids. Occasionally, the ketogenic diet may result in increased incidence of nephrolithiasis and other serious complications (Van Itallie, et al; *Ketone metabolism's ugly duckling;* Nutr Rev. 61:327-341, 2003). Some of these adverse effects can be prevented by ensuring adequate hydration; and the hyperlipidemia can be avoided by boosting the proportion of polyunsaturated and monounsaturated fats in the diet (Fuehrlein et al *Differential metabolic effects of saturated versus polyunsaturated fats in ketogenic diets;* J Clin Endocrinol Metal) 89:1641-1645, 2004). Also, the inclusion of medium-chain triglycerides (glycerol esters of fatty acids having typically 8 and/or 10 carbons in the fatty acid groups) into the ketogenic diet may improve the tolerability of the ketogenic diet (Huttenlocher et al; *Medium-Chain triglycerides as a therapy for intractable childhood epilepsy,* Neurology, Vol 11, November 1971, pp 1097-1103; Wu et al, *Medium-Chain Triglycerides in Infant Formulas and their Relation to Plasma Ketone Body Concentrations,* Pediatric Research, Vol 20, No. 4, pp 338-341; 1986; Balietti et al, *Ketogenic diets: An historical antiepileptic therapy with promising potentialities for the aging brain,* Aging Research, and Reviews 9 (2010) 273-279.

Thus, while raising ketone levels in the TBI patient is desirable, one is left with the unsuitable alternatives of use of the ketogenic diet or starvation as the choices for dietary intervention in TBI, a treatment choice which is difficult to maintain in TBI patients.

OBJECTS OF THE INVENTION

An object of the invention is to provide a method of oral/enteral dietary intervention in the treatment of traumatic brain injury (TBI) in a subject in need thereof while avoiding both of starvation and a ketogenic diet.

Another object of the invention is to provide a method of oral/enteral dietary intervention in the treatment of traumatic brain injury (TBI) in a subject in need thereof in the absence of other medical intervention for TBI while avoiding both of starvation and a ketogenic diet.

A further object of the invention is to provide a method of oral/enteral dietary intervention in the treatment of traumatic brain injury (TBI) in a subject in need thereof in addition to other medical intervention for TBI while avoiding both of starvation and a ketogenic diet.

A still further object of the invention is to provide a method of oral/enteral dietary intervention in the treatment of traumatic brain injury (TBI) in a subject in need thereof in addition to other medical intervention for TBI in conjunction with a standard enteral diet or standard parenteral feeding of a diet inclusive of a substantial portion of glucogenic calories.

Still another object of the invention is to achieve the forgoing objects by administration of a 3-hydroxybutyrate-glyceride ester in an amount of the 3-hydroxybutyroyl

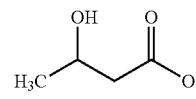

content corresponding to the oral administration of about 0.5 g/kg to 2.0 g/kg of body weight per day of glyceryl tris(3-hydroxybutyrate)

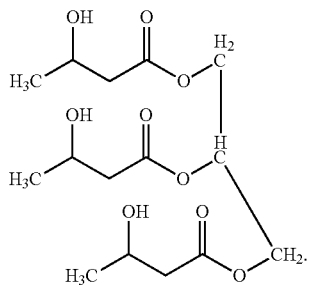 [SMILES: CC(O)CC(=O)OCC(COC(=O)CC(C)O)OC(=O)CC(C)O]

An even further object of the invention is to achieve the foregoing objects by administration of a 3-hydroxybutyroyl-glyceride ester in an amount so as to result in a total ketone body blood plasma level of about 2 to about 7.5 mM.

Yet another object of the invention is to achieve the forgoing objects by administration of the glyceryl(3-hydroxybutyrate) ester(s) in a divided dose regimen of 2-3 x/day for at least 7 days with re-evaluation for restart of the regimen at that point.

Even further objects of the invention will become apparent to those of ordinary skill in the art after having benefit of the instant application.

BRIEF SUMMARY OF THE INVENTION

In brief, the foregoing objects of the invention and others can be obtained by the administration of a glyceryl-(3-hydroxybutyrate) ester to a subject who is having or has recently had a non-penetrating closed traumatic brain injury (TBI) or a subject who has had a surgically related traumatic brain injury while maintaining a standard, normal diet that includes a substantial glucogenic caloric content. This is surprising and expected in that the literature indicates that in TBI, while there is very transient hyperutilization of glucose, this is followed by a prolonged, period of associated hyperglycemia, and that the more severe the hyperglycemia, the poorer the outcome for the patient. In addition, the literature indicates that the use of a starvation or ketogenic diet is beneficial in the treatment of TBI. Therefore, the further exacerbation of the hyperglycemia by administration of a glucogenic diet would be contraindicated. Even further, fore some conditions, such as epilepsy, the superb control of the condition when on a ketogenic diet was rapidly reversed on inclusion of a high carbohydrate meal (See Gasior et al, 2006 above). Nonetheless, the present inventor has found that contrary to the teachings of the art, the administration of the ketogenic glycerol 3-hydroxybutyrate esters can be administered in conjunction with diets that do not restrict glucogenic caloric intake such that standard oral/enteral diets can be utilized and the beneficial ketonemia arrived at in a manner that is reasonable to have TBI patients follow for significant periods, both under close medical supervision as well after release into home care. When the ester is glyceryl tris(3-hydroxybutyrate), it is administered in an amount that is typically in the range of 0.5 g/kg to 2.0 g/kg body weight per day in 2-3 divided doses, which for a 60-kg female is about 10-40 g/serving thrice daily to about 15-60 g/serving twice daily and for a 70 kg male is about 12-47 g/serving thrice daily to about 17.5-70 g/serving twice daily. These doses and serving sizes are designed to result in total ketone body blood plasma levels (combined 3-hydroxybutyrate and acetoacetate) blood plasma levels of 2 mM to 7.5 mM in an average typical subject to whom these compounds are administered. Dosings for children should be also based on the mg/kg/day range initially and modified based on the ketonemia, when such readings can be obtained. Those of ordinary skill in the art will know how to adjust these dosage amounts in subjects presenting with non-typical distribution and/or metabolisms such that the foregoing doses do not result in the blood plasma level being in the correct range. (Veterinary use (such as in mammals that are household pets, domesticated animals, farm animals, and/or zoological park animals) is also possible and those of ordinary skill will be able to adapt the dosings appropriately for the species being treated based on the various dosings set forth herein.) When the ester is one of the other esters discussed more fully below, the dose is calculated to result in a comparable blood plasma level of the combined 3-hydroxybutyroyl moiety and acetoacetate moiety that is ultimately the result of glyceryl tris(3-hydroxybutyrate) administered as stated above. (For clarity the "comparable amount" is calculated as the combined levels of 3-hydroxybutyrate groups and acetoacetate groups since 3-hydroxybutyrate is converted to acetoacetate. If using actual blood plasma levels to determine the corresponding amounts, the practitioner may choose any particular time point after administration for so choosing the readings, and one is not limited to the same time point after administration in each ester as different esters may have slightly different pharmacokinetics and may therefore have differences in lag times for the blood plasma levels to reach the appropriate range. In any event, a first approximation of the corresponding dose for esters useful in the invention that do not have three 3-hydropxybutyrate groups is to use an approximately stoichiometrically equal amount based on the 3-hdyroxybutyrate groups in the ester of choice relative to the glyceryl tris(3-hydroxybutyrate) ester.

BRIEF DESCRIPTION OF THE DRAWING

Not Applicable

DETAILED DESCRIPTION OF THE INVENTION

The present invention is directed to the use of compounds that have the 3-hydroxybutyroyl group

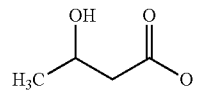

esterified to a glycerol group in the management, treatment, or prevention of one or more of the symptoms associated with the traumatic brain injury (TBI) and/or management, treatment, or prevention of the sequela thereof, and/or the underlying neurological basis for the symptoms. For the present invention purposes, "treatment" is intended to mean that administration of the glyceryl 3-hydroxybutyrate ester is as quickly after a TBI as is possible and glucogenic caloric intake is either (a) maintained at normal levels for the patient in question or (b) restricted to a typical standard enteral diet which contains a substantial percentage of glucogenic caloric content and which excludes a starvation diet and excludes a ketogenic diet having less than 2% carbohydrate and less than 8% protein by weight, preferably excluding a diet having not more than 2% carbohydrate and not more than 8% protein by weight; more preferably excluding a diet less than 10% carbohydrate and less than 15% protein by weight, most preferably excluding a diet having not more than 10% carbohydrate and not more than 15% protein by weight. The oral/enteral feedings of the above diet can be begun at any time that would be normal for the next meal after the patient presents, or may be initially administered immediately with or closely following the administration of the glycerol 3-hdyroxybutyrate ester as may be desired.

In many cases, the TBI is the result of an accident (vehicle or otherwise), a sports injury, or military action, etc. For purposes of the present invention. TBI is deemed to be brain injuries that are non-penetrating and closed but do include surgical injuries (notwithstanding that they are open rather than closed), and further exclude brain injuries due to stroke or aneurism, and still further exclude injuries of viral, bacterial, fungal, or prion origins. A further subset of TBI is found in Sports Related Concussion, which affects not only athletes in the TBI prone sports, but many adults and children as well. (See http://www.merckmanuals.com/professional/injuries-poisoning/traumatic-brain-injury-tbi/sports-related-concussion.) Another large set of TBI patients are those serving in the military and in security forces. Such personnel are frequently in danger of suffering TBIs of all kinds due to the dangerous nature of the roles in combat and exposure to Improvised Explosive Device land mines, artillery, etc.

In many TBI instances where the esters for use in the invention are available, they can be administered in the field as soon as the injured party is able to orally ingest the esters. This can be administered by medical or non-medical personnel where desired. If the esters for use in the present invention are not available in the place where the injury took place, they can be administered on arrival of medical personnel such as by an EMT before or during transit to a facility or before the patient declines transport, or as soon as possible upon arrival at a medical facility. Since the glyceryl 3-hydroxybutyrate ester is administered by mouth, the only limitation on the above is that the patient be able to ingest the ester orally. If a feeding tube is needed, the ester can be administered in a suitable form through the feeding tube once such a tube is properly inserted.

The esters can be those in which 3-hydroxybutyroyl groups

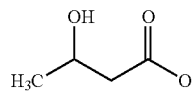

esterify 1, 2, or all 3 of the hydroxy groups in a single glycerol molecule. When less than all three of the glycerol hydroxy groups are esterified by the 3-hydroxybutyroyl group, the remaining glycerol hydroxy groups can remain unesterified, be esterified by omega-3-fatty acids, omega-6-fatty acids, omega-3,6-fatty acids, medium-chain fatty acids or mixtures thereof. (Medium-chain fatty acids are fatty acids having carbon chains of generally 8 and/or 10 carbons, such as for example, one such medium-chain fatty acid in a purified form is caprylic acid.) Each 3-hydroxybutyroyl group in each molecule is independently in either D or L form and the bulk compound being administered can be a mix of any or all of the same (i.e. a mix of compounds having (a) all of the groups in the D form, (b) all of the groups in the L form, (c) some in the D-form and some in the L-form, (d) as well as mixtures of compounds selected from (1) a and b, (2) a and c, and (3) a, b, and c). Both the D and L forms of the 3-hydroxybutyroyl groups are active, however, the L form is utilized more slowly and thus, it is preferable that the 3-hydroxybutyroyl groups are substantially all in the D form. In a particularly preferred embodiment, about 90% to 98%, more preferably about 96% of the 3-hydroxybutyroyl groups are in the D form. Nonetheless, utilization of other amounts of D vs L forms are within the invention and can be selected from 100% D to 100% L and any mixture of D and L forms in any proportions. In addition, mixtures of esters having one, two, or 3 (3-hydroxybutyryl) groups with (a) no other esterification or (b) further esterification with an omega fatty acid (either 3-omega, 6-omega, or 3,6-omega or mixtures thereof) or (c) further esterified with a mid-chain fatty acid or mixtures of different mid-chain fatty acids or (d) further esterified with both an omega fatty acid and a mid-chain fatty acid are also contemplated to be within the scope of compounds for use in the present invention. A highly preferred embodiment is one in which the compound utilized for the present invention is glyceryl tris(3-hydroxybutyrate); an even more highly preferred compound is glyceryl tris(DL 3-hydroxybutyrate), the DL referring to the bulk-compound and not necessarily a mixture in a specific molecule; and a still more highly preferred embodiment is in the use of glyceryl tris(D96%/L4% 3-hydroxybutyrate), D96%/L4% referring to the bulk compound and not necessarily a mixture in a specific molecule. These compounds and a method of manufacture thereof are described more fully in U.S. Pat. No. 7,807,718, which is incorporated herein concerning the description of the compounds and their manufacture.

In brief, the foregoing object of the invention and others can be obtained by the administration of a glyceryl-(3-hydroxybutyrate) ester to a subject who has suffered a TBI, the TBI may range from severe enough to require additional medical intervention to mild enough that no further medical intervention is deemed necessary, the mildest forms not showing overt symptoms that the patient is aware of, but which evidence of characteristic changes in blood chemistry and other tests indicate that a mild injury has in fact occurred. As such, the present invention is also suitable as a prophylactic treatment in patients that have sustained a head injury where the overt physical symptoms to the patient are so slight as to not being recognized. In general, the clinical evaluation as to the severity of the injury is determined by the Glasgow Coma Scale (adults) and the Modified Glasgow Coma Scale (for infants and children). (See Merck Manual Professional Version, online at http://www.merckmanuals.com/professional/injuries-poisoning/traumatic-brain-injury-tbi/traumatic-brain-injury; last updated October 2013. and Teasdale; *Assessment of Coma and Impared Consciousness: A Practical Scale,* The Lancet, Jul. 13, 1974, pp. 81-84.) Notwithstanding the foregoing, in general, any patient suffering a head trauma sufficient to be considered a concussive patient is a suitable patient for the present invention treatment, provided oral ingestion of the ester and diet is suitable or suitable by feeding tube. While the esters of use in the present invention are administered orally, the nutritional diet being administered can be either orally by normal ingestion, enterally via a feeding tube, or may be parenterally, where desired.

When the ester is glyceryl tris(3-hydroxybutyrate), it is generally orally/enterally administered in an amount that is typically in the range of 0.5 g/kg to 2.0 g/kg body weight per day (more specifically 0.5 g/kg, 0.55 g/kg, 0.6 g/kg, 0.65 g/kg, 0.7 g/kg, 0.75 g/kg, 0.8 g/kg, 0.85 g/kg, 0.9 g/kg, 0.95 g/kg, 1 g/kg, 1.1 g/kg, 1.2 g/kg, 1.3 g/kg, 1.4 g/kg, 1.5 g/kg, 1.6 g/kg, 1.7 g/kg, 1.8 g/kg, 1.9 g/kg, or 2 g/kg, as well as amounts intermediary between any of these specifically recited amounts) in 2-3 divided doses, which for a 60 kg female is about 10-40 g/serving (more specifically 10 g/serving, 12.5 g/serving, 15 g/serving, 17.5 g/serving, 20 g/serving, 22.5 g/serving, 25 g/serving, 30 g/serving, 35 g/serving, 40 g/serving as well as amounts intermediary between any of these specifically recited amounts) thrice daily (approximately every 8 hours) to about 15-60 g/serving (more specifically 15 g/serving, 17.5 g/serving, 20 g/serving, 22.5 g/serving, 25 g/serving, 27.5 g/serving, 30 g/serving, 35 g/serving, 40 g/serving, 45 g/serving, 50 g/serving, 55 g/serving, or 60 g/serving as well as amounts intermediary between any of these specifically recited amounts) twice daily (approximately every 12 hours) and for a 70 kg male is about 12-47 g/serving (more specifically 12 g/serving, 15 g/serving, 17.5 g/serving, 20 g/serving, 22.5 g/serving, 25 g/serving, 30 g/serving, 35 g/serving, 40 g/serving, 45 g/serving, 47 g/serving, as well as amounts intermediary between any of these specifically recited amounts) thrice (approximately every 8 hours) daily to about 17.5-70 g/serving (more specifically 17.5 g/serving, 20 g/serving, 22.5 g/serving, 25 g/serving, 27.5 g/serving, 30 g/serving, 35 g/serving, 40 g/serving, 45 g/serving, 50 g/serving, 55 g/serving, 60 g/serving, 65 g/serving, 70 g/serving, as well as amounts intermediary between any of these specifically recited amounts) twice (approximately every 12 hours) daily. These doses and serving sizes are intended to result in total ketone body (combined 3-hydroxybutyrate and acetoacetate) blood plasma levels of 2-7.5 mM (more specifically 2 mM, 2.25 mM, 2.5 mM, 2.75 mM, 3 mM, 3.25 mM, 3.5 mM, 4 mM, 4.25 mM, 4.5 mM, 4.6 mM, 4.7 mM, 4.8 mM, 4.9 mM 5.0 mM, 5.1 mM, 5.2 mM, 5.3 mM, 5.4 mM, 5.5 mM, 5.6 mM, 5.7 mM, 5.8 mM, 5.9 mM, 6.0 mM, 6,1 mM, 6.2 mM, 6.3 mM, 6.4 mM, 6.5 mM, 6.6 mM, 6.7 mM, 6.8 mM, 6.9 mM, 7.0 mM, 7.1 mM, 7.2 mM, 7.3 mM, 7.4 mM, 7.5 mM as well as intermediary levels between any of these specifically recited levels and any of these may serve as a lower end of a range or upper end of a range provided the upper end of the range is larger than the lower end of that range) in an average typical subject to whom these compounds are administered. (Acetoacetate is an oxidized form of 3-hydroxybutyrate in which the 3-hydroxy group is replaced by a 3-oxo group

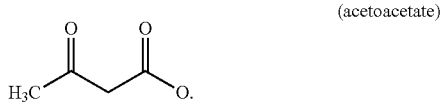

(acetoacetate)

When the esters used in the present invention are ingested orally, the esters are primarily hydrolyzed in the intestinal tract due to pancreatic lipase, releasing the 3-hydroxybutyrate moiety which is absorbed, and the body utilizes the 3-hydroxybutyrate by converting it to acetoacetate which, turn, is actually used by the cells.) Those of ordinary skill in the art will know how to adjust these dosage amounts in subjects presenting with non-typical distribution and/or metabolisms such that the foregoing doses do not result in the blood plasma level being in the correct range. (Such modified amounts that are administered are considered within the scope of the invention if they raise the combined blood plasma level of 3-hydroxybutyrate and acetoacetate into the range of 2 mM to 7.5 mM range, notwithstanding they are outside of the "serving size" ranges or bulk g of compound administered set forth elsewhere in this specification.) When the ester is one of the other esters discussed more fully below, the dose is calculated to deliver a comparable amount of the combined 3-hydroxybutymyl and acetoacetate moieties that is ultimately delivered by the glyceryl tris(3-hydroxybutyrate).

In the present specification, in any case where a range of values for a particular parameter is given and a more specific recitation of values within such range is given each specific value can be the basis for a new range limit as long as the lower limit is in fact less than the upper limit. By way of example, in the foregoing paragraph, the dosage range is given as "0.5 g/kg to 2.0 g/kg" with a more specific recitation of "0.5 g/kg, 0.55 g/kg, 0.6 g/kg, 0.65 g/kg, 0.7 g/kg, 0.75 g/kg, 0.8 g/kg, 0.85 g/kg, 0.9 g/kg, 0.95 g/kg, 1 g/kg, 1.1 g/kg, 1.2 g/kg, 1.3 g/kg, 1 4 g/kg, 1.5 g/kg, 1.6 g/kg, 1.7 g/kg, 1.8 g/kg, 1 9 g/kg, or 2 g/kg". Based thereon, any of the more specific recited amounts may be the lower limit of a new range and any larger specific recited amount may be the upper limit of that new range and each such constructed range shall be deemed as specifically recited in this specification. As such, by way of example and not limitation, the ranges of 0.5 to 0.6; 0.55 to 1.9, 0.75 to 1.7, 1.8 to 1.9, etc. are all deemed recited herein. The same is applicable to the other parameters relating to dosages based on body weight, serving sizes, etc. as well.

The ester compounds for use in the present invention are administered in amounts that deliver the same amount of 3-hydroxybutyroyl and/or acetoacetate moiety as that when 0.5 g/kg to 2.0 g/kg body weight of the glyceryl tris(3-hydroxybutyrate) is administered orally. Again, the focal point to achieve the appropriate ketone body (3-hydroxybutyroyl level plus acetoacetate level) in the blood plasma of between 2 mM and 7 mM, preferably 4.5 mM to 7 mM, more preferably 5 mM to 7 mM. In cases where the actual volume or weight of this amount is too cumbersome or undesired to give as a single dose, the dose can be divided into multiple divided doses of desirable size given multiple times per day or in multiple dosage units given in a single dose (i.e. within a few moments of one another as desired). Preferably the dose is divided into 2-3 divided doses, spaced apart approximately equally over the course of a 24-hour period, so that twice daily dosing is approximately every 12 hours and thrice daily dosing is approximately every 8 hours. By way of example, if 50 g is desired to be administered, it can be done as a single dose of 50 g in a single dosage form or distributed in a food or drink or it can be administered in ½ such amounts twice daily, or it can be administered in a dosage form having ½ the dose in two dosage units given within a few moments of one another (preferably within a few seconds of one another when a substantially single dosing is desired). Where multiple dosings per day are desired or multiple dosage units per day at a single dosing are desired, other fractional closings and multiple dosage units will be known to those of ordinary skill in the art and include without limitation administration of ⅓ the above amounts administered 3 times a day or in three units administered at substantially the same time; ¼ the above amounts administered 4 times a day or in four units administered at substantially the same time or 2 units twice in a day, etc. The intent and objective is to induce a therapeutic hyperketonemia characterized by blood plasma levels of the 3-hydroxybutyroyl group

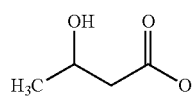

(together with the acetoacetate group) of 2 mM-7.5 mM, (such as 4.5 mM, 5.0 mM, 5.5 mM, 6.0 mM, 6.5 mM, 7.0 mM or 7.5 mM, and all mM levels between any particular of these explicitly recited amounts is deemed to be explicitly disclosed as well) comparable to those achieved by ketogenic diet or starvation. Those of ordinary skill in the an will appreciate other variations on the theme.

Generally, upon oral administration, the necessary blood plasma ketone body levels can be achieved within 24 hours, more usually within 12 hours, even more typically within 6 hours, even more typically within 2 hours, yet more likely within 1 hour. On oral administration, the ketone body blood plasma levels rise quickly and peak in about 30 minutes or 45 minutes to 1 hour. Once administration has begun, administration should continue in daily fractional doses twice or three times a day (½ the daily dose twice daily or ⅓ the daily dose three times a day) or even smaller fractional doses more frequently on a daily basis for about 7 days after which, the patient should be re-evaluated and if deemed necessary the regimen restarted for another 7 days, with a further re-evaluation. If desired, re-evaluations can be performed at shorter or longer durations depending upon the clinical outcome, but the treatment should be for at least 7 days after the injury.

As previously stated, the above dosing range of the glyceryl tris( 3-hydroxybutyrate) is expected to provide a total ketone body blood plasma level (3-hydroxybutyroyl group $$\underset{H_3C}{\overset{OH}{\diagup}}\underset{}{\diagdown}\underset{}{\overset{O}{\diagup}}\underset{O}{\diagdown}$$

and acetoacetate) of 2 mM to 7 mM.

EXAMPLES

The following examples exemplify, but do not limit, the present invention.

Example 1

A 60 kg female presents with TBI due to a minor car accident. On initial examination, within 1 hour of the accident, moderate TBI is determined by EMT at the scene, on the basis disorientation and of the Glasgow Coma Scale (9-13). The patient is conscious, is hyperglycemic and able to orally ingest the ester. The patient is started on 0.5 g/kg/day glyceryl tris(3-hydroxybutyrate) orally in 3 divided doses (i.e., 10 g per serving 3 times a day). The patient is transported to a medical facility and allowed to ingest a standard diet lunch, having no glucogenic caloric restriction. After 2 days, the patient appears to have recovered from her disorientation, is released and advised to continue self-administration of the glyceryl tris(3-hydroxybutyrate) for an additional 5 days, while continuing to eat her normal meals, and to return for re-evaluation at that time. The patient completes the regimen. The patient is followed up on completion of the regimen (at day 7 on the regimen) and appears to be fully recovered. Surprisingly, the patient remains euglycemic from shortly after the ester administration through the end of treatment and beyond.

Example 2

A second 60 kg female presents with TBI due to a minor car accident. On initial examination, within 1 hour of the accident, moderate TBI is determined by EMT at the scene, on the basis of disorientation and of the Glasgow Coma Scale (9-13). The patient is hyperglycemic, conscious and able to orally ingest the food and medication. The patient is started on a ketogenic diet in order to induce ketone elevation and reduce her hyperglycemia. The patient although still being somewhat disoriented, is moderately hypoglycemic and is released after 2 days to a caregiver who can observe for worsening symptoms and is directed to continue on the ketogenic diet for 5 more days and return for re-evaluation. The patient abandons the ketogenic diet almost immediately after being released. The patient is followed up on what should have been the $7^{th}$ day of ketogenic diet and although not diabetic, shows improper glycemic control, appears to be have residual disorientation, and shows signs of post-concussion syndrome.

Example 3

A 70 kg male (boxer) presents with a sports injury concussion after having a history of 3 similar concussions over the past year. The past concussions are treated by standard medical practice without the use of ketogenic diet, starvation, or the esters of use in the present invention. The most recent concussive injury occurs 2 hours before the patient being brought into a hospital for treatment. The patient is immediately examined and determined to be hyperglycemic and to have a moderate concussive injury (on the basis of short term loss of consciousness, his lingering disorientation, and a Glasgow Coma Scale score of 9-13). The patient is started on 2.0 g/kg/day glyceryl tris(3-hydroxybutyrate) in three divided dose (i.e.. 46.7 g per serving 3 times a day) and permitted an ordinary standard oral diet not having glucogenic caloric restrictions for a 70 kg male. Treatment continues for 3 days. On evaluation at that tine, the patient appears to have recovered from his disorientation, and is released and told to self-administer the glyceryl tris(3-hydroxybutyrate) for an additional 4 days and return for re-evaluation. The patient continues and completes the regimen and is followed up on day 7 of the prescribed regimen and is fully recovered. Surprisingly, the patient is euglycemic from shortly after the ester administration through the end of treatment.

Example 4

A 70 kg male (boxer) presents with a sports injury concussion after having a history of 3 similar concussions over the past year. The past concussions are treated by standard medical practice without the use of ketogenic diet, starvation, or the esters of use in the present invention. The most recent concussive injury occurs 2 hours before the patient being, brought into a hospital for treatment. The patient is immediately examined and determined to be hyperglycemic and to have a moderate concussive injury (on the basis of short term loss of consciousness, his lingering disorientation, and a Glasgow Coma Scale score of 9-13). The patient is started on a ketogenic diet. Treatment continues for 3 days upon which the patient is found to be hypoglycemic, has reduced the level of disorientation from initial presentation somewhat, is released into the custody of a caregiver who can monitor the patient for worsening of symptoms, and told maintain the ketogenic diet for an additional 4 days and return for re-evaluation. The patient promptly abandons the ketogenic diet regimen. On follow up on the supposed $7^{th}$ day of ketogenic diet, the patient has improper glycemic control, shows signs of continued disorientation, and shows signs of post-concussive syndrome.

Example 5

A 70 kg male (boxer) presents with a sports injury concussion after having a history of 3 similar concussions over the past year. The past concussions are treated by standard medical practice without the use of ketogenic diet, starvation, or the esters of use in the present invention. The most recent concussive injury occurs 2 hours before the patient being brought into a hospital for treatment. The patient is immediately examined and determined to be hyperglycemic, to have a moderate concussive injury (on the basis of short term loss of consciousness, his lingering disorientation, and a Glasgow Coma Scale score of 9-13). The patient is started on a starvation diet. Treatment continues for 3 days, found to be hypoglycemic, has a somewhat reduced level of disorientation from initial presentation, is and is released into the custody of a caregiver who can monitor the patient for worsening of symptoms, and told to maintain the starvation diet for an additional 4 days and return for re-evaluation. The patient abandons the regimen immediately. On follow up on what would have been the $7^{th}$ day of starvation, the patient has improper glycemic control, shows signs of continued disorientation, and shows signs of post-concussive syndrome.

Example 6

The patient in Example 3, knowing that further concussive incidents are likely requests advice as to minimizing the effects of further concussive incidents. The patient is told to restart the glyceryl tris(3-hydroxybutyrate) regimen at least one meal period before partaking in the activity likely to result in a concussive injury. The patient has such serving at a 5 PM dinner and is in a match at 7 PM. The patient does in fact suffer a further TBI which once again is upon examination at the scene is determined to be a moderate TBI, however, the patient is euglycemic. On transport to a medical facility, the patient is re-examined and confirm that he has suffered another moderate TBI. The patient is started on 2.0 g/kg/day glyceryl tris(3-hydroxybutyrate) in three divided doses 46.7 g per serving 3 times a day) and permitted an ordinary standard oral diet not having glucogenic caloric restrictions for a 70 kg male. The next day, the patient is alert, shows no adverse effects, and has a Glasgow Coma Scale score in in excess of 15, and is released. The patient is advised to continue with the glyceryl tris(3-hydroxybutyrate) regimen as in Example 3 for 6 days and return for re-evaluation. The patient maintains the regimen for 3 days instead of the recommended 6 and reports no adverse or lingering effects from the TBI. On reexamination, no symptoms are seen.

Example 7

The patients in Examples 2, 4, and 5 on re-evaluation are immediately started on the regimens referred to in Examples 1, 3, and 3 respectively for 7 days, and directed to return for re-evaluation on the $7^{th}$ day of the newly started regimen. Each of the patients completes the regimen and shows improvement in the parameter that remains deficient in the evaluation after what should have been the $7^{th}$ day of ketogenic diet or starvation. However, the improvement is not as complete as the patients in Examples 1 or 3.

Example 8

A 30 kg child is brought to the emergency room with moderate to severe TBI (as per the Modified Glasgow Coma Scale) due to a playground fall, is hyperglycemic, is unconscious, is intubated, and begun on a regimen of 30 g twice daily of glyceryl tris(3-hydroxybutyrate) and further fed standard normal enteral diet. The regimen is continued for 7 days and re-evaluated at that time. The patient's clinical symptoms show improvement, but are not yet in normal ranges. The treatment is continued, with re-evaluation set for 7 days later. On day 4, the child regains consciousness and is re-evaluated at that time. While the clinical evaluation appears normal, the treatment is continued for an additional 3 days after which the child appears fully recovered and is released with no further treatment.

Example 9

Patients presenting with moderate TBI are treated upon diagnosis with administration of the glyceryl tris(3-hydroxybutyrate) in accordance with the invention along with normal meals 2 or 3 times a day for one or two weeks, and compared with matched patients presenting with TBI that are treated with ketogenic diets (which patients do not continue for the full treatment recommendation) or starvation (which the patients do not follow for the full treatment recommendation). The patients are followed up approximately 6 months, after the TBI. Long term effects in the TBI patients treated according to the present invention are minimal, if not non-existent. In patients that are started on starvation or ketogenic diet, but do not complete the full regimen course, but then are transitioned to the present invention regimen within a short time, long term effects are seen in a greater extent. In patients that are started on a ketogenic diet or starvation and do not complete the full regimen and do not transition to the present invention regimen, long term effects of TBI are seen to an even greater extent, almost approximating the degree and severity seen in those that historically do receive any treatment.

Example 10

Military personnel having closed TBIs due to vehicular accidents or IEDs or other battlefield causes are evaluated for the severity of their TBIs and, where glyceryl tris(3-hydroxybutyrate) is available for administration, are started on a regimen of 0.5 mg/kg/day to 2.0 mg/kg/day in 2 or 3 divided doses for 7 days (which regimen is generally started within 2 or 3 hours of injury) and then re-evaluated at day 7 to assess whether further treatment for the TBI is warranted. These are compared with comparably injured military personnel where access to the glyceryl tris(3-hydroxybutyrate) was not available for administration within the first week after injury. When matching subjects for degree of injury, comparisons show that those receiving the glyceryl tris (3-hydroxybutyrate) fare much better than those not receiving it, both in recovery from acute symptoms as well as in long-term post-concussive syndrome symptoms.

Example 11

In light of Example 10, combat troops and medics associated therewith are provided with glyceryl tris(3-hydroxybutyrate) to take into the field for use in triage in the case of mild-moderate closed TBI situations. When viewed against Example 10, those TBI patients receiving the glyceryl tris(3-hydroxybutyrate) within minutes of suffering the TBI fare even better than those receiving the glyceryl tris(3-hydroxybutyrate) treatment in Example 10.

Example 12

In light of Examples 10 and 11, combat troops are routinely given a morning dose of glyceryl tris(3-hydroxybutyrate) while in combat zones in case they suffer a mild to moderate non-penetrating closed TBI. For those troops that do suffer such TBIs within 12 hours of administration, their recovery, both acutely and longer term, is improved as compared to those only receiving the glyceryl tris(3-hydroxybutyrate) administration upon injury, after being matched for injury severity. Similar comparatives between those getting variously identical regimens of glyceryl tris (3-hydroxybutyrate) post-injury other than the single prophylactic dose prior to injury, with those receiving the preinjury dose faring better than those not receiving it, and further those whose injury is closer in time to the administration (1-2 hours post administration) faring better than those being injured further in time form the administration (10-12 hours post-administration).

The invention claimed is:

1. A method of reducing damage from a mild to moderate non-penetrating, closed traumatic brain injury, hereafter referred to as "TBI", in a human subject, said human subject having a history of at least one prior TBI,
    said method comprising oral administration of a glyceryl tris (3-hydroxybutyrate) ester in which each of said 3-hydroxybutyrate group in said glyceryl tris (3-hydroxybutyrate ester is independently selected from the group consisting of D-3-hydroxybutyrate and L-hydroxybutyrate, including mixtures of said esters;
    said administration being in an amount of said glyceryl tris (3-hydroxybutyrate) ester so as to result in a total ketone body blood plasma level defined as the sum of said subject's blood plasma levels of 3-hydroxybutyroyl moiety and acetoacetate moiety and which is within a range of 2 mM to 7.5 mM;
    said administration is conducted in conjunction with maintaining a normal diet, said normal diet having greater than 10% carbohydrate and greater than 15% protein;
    said TBI, once occurring, having additionally associated therewith, in the absence of said administration or other medicinal intervention, a transient hyper-utilization of glucose phase followed by a persistent hyperglycemia;
    whereby if said TBI occurs to said human subject within 12 hours of said administration, said blood plasma level of said human subject is within said range when said TBI occurs and said damage from said TBI is reduced.

2. The method of claim 1 wherein said 3-hydroxybutyrate moiety in said glyceryl tris (3-hydroxbutyrate) ester is in the D-form.

3. The method of claim 1 wherein each said 3-hydroxybutyrate moiety in said glyceryl tris (3-hydroxybutyrate) ester is in the L-form.

4. The method of claim 1 wherein at least a portion of said glyceryl tris (3-hydroxybutyrate) ester is a mixed DL ester, designated glyceryl tris (DL-3-hydroxybutyrate ester, wherein at least one 3-hydroxybutyrate moiety of said glyceryl tris (DL-3-hydroxybutyrate) ester is in the D-form and at least one 3-hydroxybutyrate moiety of said glyceryl tris (DL-3-hydroxybutyrate) ester is in the L-form.

5. The method of claim 1 wherein said amount is further selected from an oral amount of about 0.5 g/kg of body weight/day to about 2.0 g/kg of body weight/day of said glyceryl tris (3-hydroxybutyrate) ester, taken as a single serving prior to said human subject participating in said activity of one-third to one-half of said daily amount such that if said further TBI occurs within 12 hours of said administration, said ketone body blood level is in the range of 2 mM to 7.5 mM at the point in time when said further TBI occurs.

6. The method of claim 1 wherein said total ketone body blood plasma level is achieved within the first 6 hours after said administration of said glyceryl (3-hydroxybutyrate) ester.

7. The method of claim 1 wherein said total ketone body blood plasma level is achieved within the first 2 hours after said administration of said glyceryl (3-hydroxybutyrate) ester.

8. The method of claim 1 wherein said total ketone body blood plasma level is achieved within the first 1 hour after said administration of said glyceryl (3-hydroxybutyrate) ester.

9. The method of claim 1 wherein, said total ketone body blood plasma level is achieved within the first 45 minutes after said administration of said glyceryl (3-hydroxybutyrate) ester.

* * * * *